(12) United States Patent
Liu

(10) Patent No.: US 11,246,999 B2
(45) Date of Patent: *Feb. 15, 2022

(54) ELECTRONIC CIGARETTE

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 484 days.

This patent is subject to a terminal disclaimer.

(21) Appl. No.: 16/265,981

(22) Filed: Feb. 1, 2019

(65) Prior Publication Data

US 2019/0289912 A1  Sep. 26, 2019

(30) Foreign Application Priority Data

Mar. 24, 2018 (CN) .......................... 201820404147.0
Nov. 6, 2018 (CN) .......................... 201811310499.0

(51) Int. Cl.
| | |
|---|---|
| *A61M 11/04* | (2006.01) |
| *A24F 7/00* | (2006.01) |
| *A61M 15/06* | (2006.01) |
| *H01M 50/209* | (2021.01) |
| *A24F 40/40* | (2020.01) |
| *A24F 40/10* | (2020.01) |

(52) U.S. Cl.
CPC .............. *A61M 11/042* (2014.02); *A24F 7/00* (2013.01); *A24F 40/40* (2020.01); *A61M 15/06* (2013.01); *H01M 50/209* (2021.01); *A24F 40/10* (2020.01); *A61M 2205/8206* (2013.01); *H01M 2220/30* (2013.01)

(58) Field of Classification Search
None
See application file for complete search history.

(56) References Cited

U.S. PATENT DOCUMENTS

2017/0202268 A1* 7/2017 Li .......................... A24F 40/485

* cited by examiner

*Primary Examiner* — Francisco W Tschen
*Assistant Examiner* — Guy F Mongelli
(74) *Attorney, Agent, or Firm* — Matthias Scholl P.C.; Matthias Scholl

(57) ABSTRACT

An electronic cigarette, including an atomizing assembly and a battery assembly. The atomizing assembly is disposed on the battery assembly. The atomizing assembly includes a mouthpiece cover, a mouthpiece, a seal holder, a first seal ring, an atomizing core, a silica ring, a first fixed seat, a joint, an insulation seat, a regulating ring, a fixed screw, an e-liquid container, an e-liquid feeder, a second seal ring, a first spring, an e-liquid guider, and a plug. The battery assembly includes a button, a decoration cover, second springs, switch buttons, a decoration ring, a button cap, a light guide, a second fixed seat adapted to fixing a printed circuit board, output electrodes, a third seal ring adapted to seal the output electrodes, third springs, fixed rings adapted to fix the output electrodes, a silica plug, a mainboard, a battery cell, and a base support.

1 Claim, 5 Drawing Sheets

ELECTRONIC CIGARETTE

CROSS-REFERENCE TO RELATED APPLICATIONS

Pursuant to 35 U.S.C. § 119 and the Paris Convention Treaty, this application claims foreign priority to Chinese Patent Application No. 201820404147.0 filed Mar. 24, 2018, and to Chinese Patent Application No. 201811310499.0 filed Nov. 6, 2018. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

This disclosure relates to an electronic cigarette.

Electronic cigarettes atomize nicotine-containing e-liquid.

Conventionally, the atomizing assembly fixedly communicates with the battery assembly. This increases the difficulty in replacing the atomization core. In addition, the atomizing core tends to slide out in the process of regulating the volume flow rate of the vapor. This increases the risk of unwanted leakage of the e-liquid.

SUMMARY

The disclosure provides an electronic cigarette.

Provided is an electronic cigarette, comprising an atomizing assembly and a battery assembly. The atomizing assembly is disposed on the battery assembly. The atomizing assembly comprises a mouthpiece cover, a mouthpiece, a seal holder, a first seal ring, an atomizing core, a silica ring, a first fixed seat, a joint, an insulation seat, a regulating ring, a fixed screw, an e-liquid container, an e-liquid feeder, a second seal ring, a first spring, an e-liquid guider, and a plug. The battery assembly comprises a button, a decoration cover, second springs, switch buttons, a decoration ring, a button cap, a light guide, a second fixed seat adapted to fixing a printed circuit board, output electrodes, a third seal ring adapted to seal the output electrodes, third springs, fixed rings adapted to fix the output electrodes, a silica plug, a mainboard, a battery cell, and a base support.

The first seal ring is disposed on the seal holder; the seal holder is inserted in the mouthpiece; the joint is fixed on the insulation seat; the insulation seat is disposed in the first fixed seat; the silica ring and the regulating ring are disposed on the first fixed seat; the atomizing core is inserted in the first fixed seat; the fixed screw is disposed on a bottom wall of the e-liquid container; the mouthpiece is disposed on the e-liquid container; the mouthpiece cover is disposed on the mouthpiece; the first fixed seat is fixed on the fixed screw.

The second seal ring and the first spring are disposed on one end of the e-liquid feeder, and the e-liquid guider is disposed on the other end of the e-liquid feeder; the e-liquid feeder is fixed on the e-liquid container; the plug is inserted in the e-liquid container; and the mouthpiece cover covers the e-liquid container; the regulating ring comprises locating slots, and the first fixed seat comprises stop pins corresponding to the locating slots.

The second springs are disposed in the switch buttons, and the switch buttons are fixed on two sides of the second fixed seat; the button cap is disposed in the decoration ring; and the decoration ring is fixed on the switch buttons; the mainboard and the battery cell are disposed in the base support; the third seal ring and the third springs are disposed on the output electrodes; the output electrodes are fixed on the second fixed seat via the fixed rings; the second fixed seat is disposed in the base support; and the decoration cover is attached to the second fixed seat; the silica plug is disposed on the mainboard; the light guide is disposed in the button, and the button is fixed on the second fixed seat.

Advantages of the electronic cigarette according to embodiments of the disclosure are summarized as follows. The atomizing assembly communicates with the battery assembly via the switch buttons disposed at two sides of the battery assembly. This simplifies the dismantling of the electronic cigarette and facilitates the replacement of the atomizing assembly. The regulating ring comprises locating slots, and the first fixed seat comprises stop pins corresponding to the locating slots, so that in the process of regulating the volume flow rate of the vapor, the atomization core will not detach, preventing the unwanted leakage of the e-liquid.

DETAILED DESCRIPTION

To further illustrate, embodiments detailing an electronic cigarette are described below. It should be noted that the following embodiments are intended to describe and not to limit the disclosure.

Figure 1:
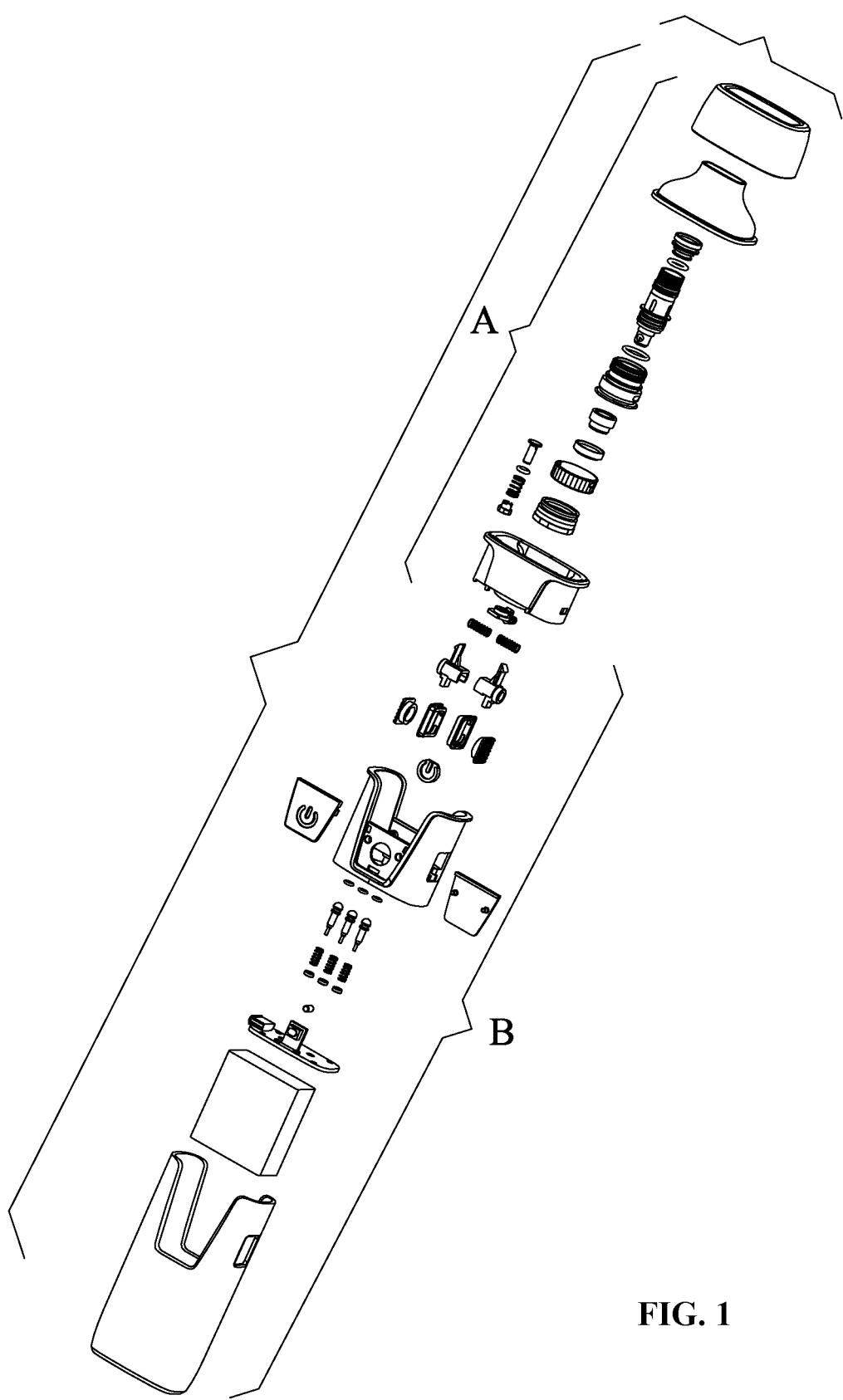
FIG. 1 is an exploded view of an electronic cigarette as described in the disclosure.
Figure 2:
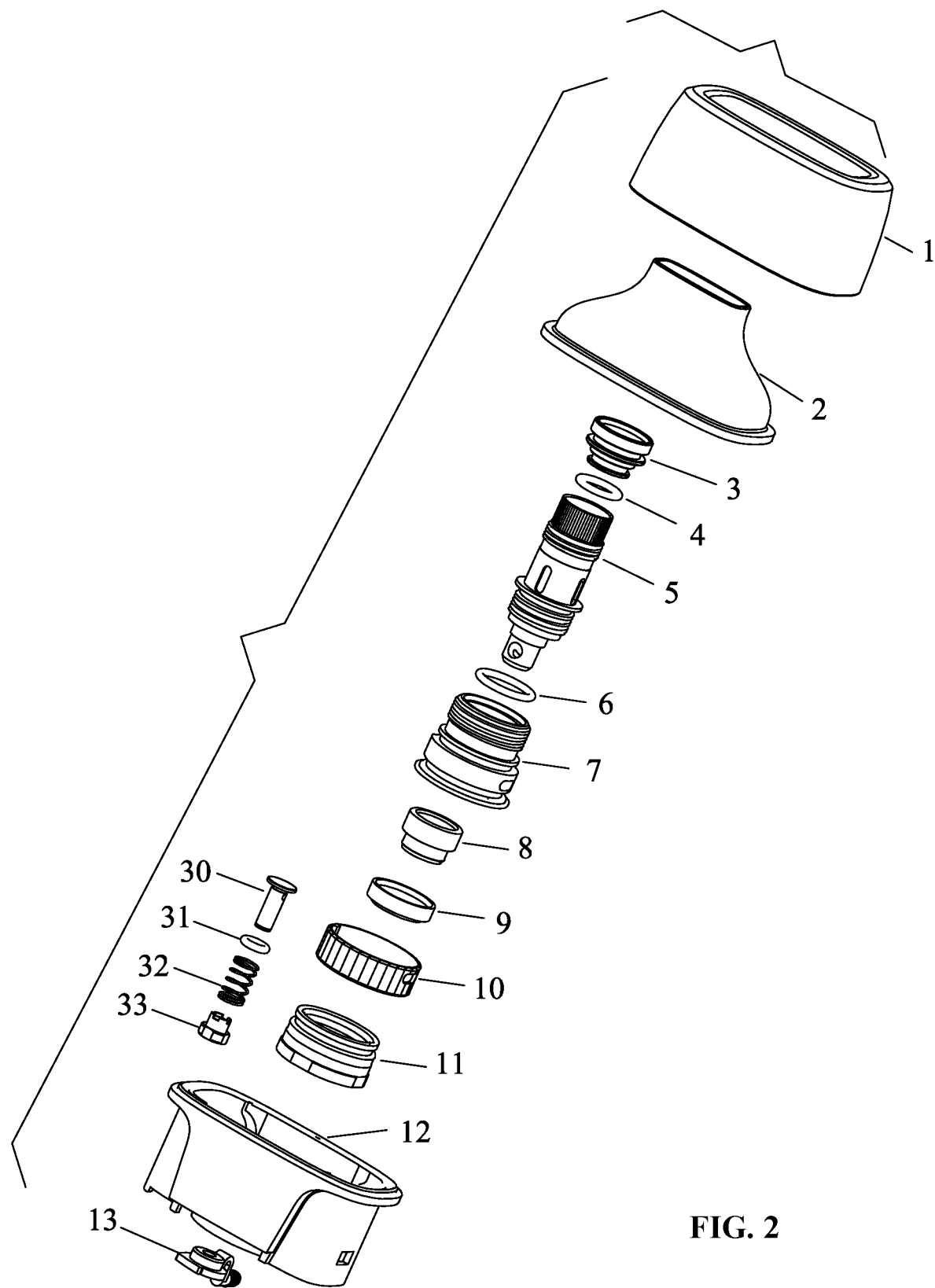
FIG. 2 is an exploded view of an atomizing assembly of an electronic cigarette as described in the disclosure.
Figure 3:
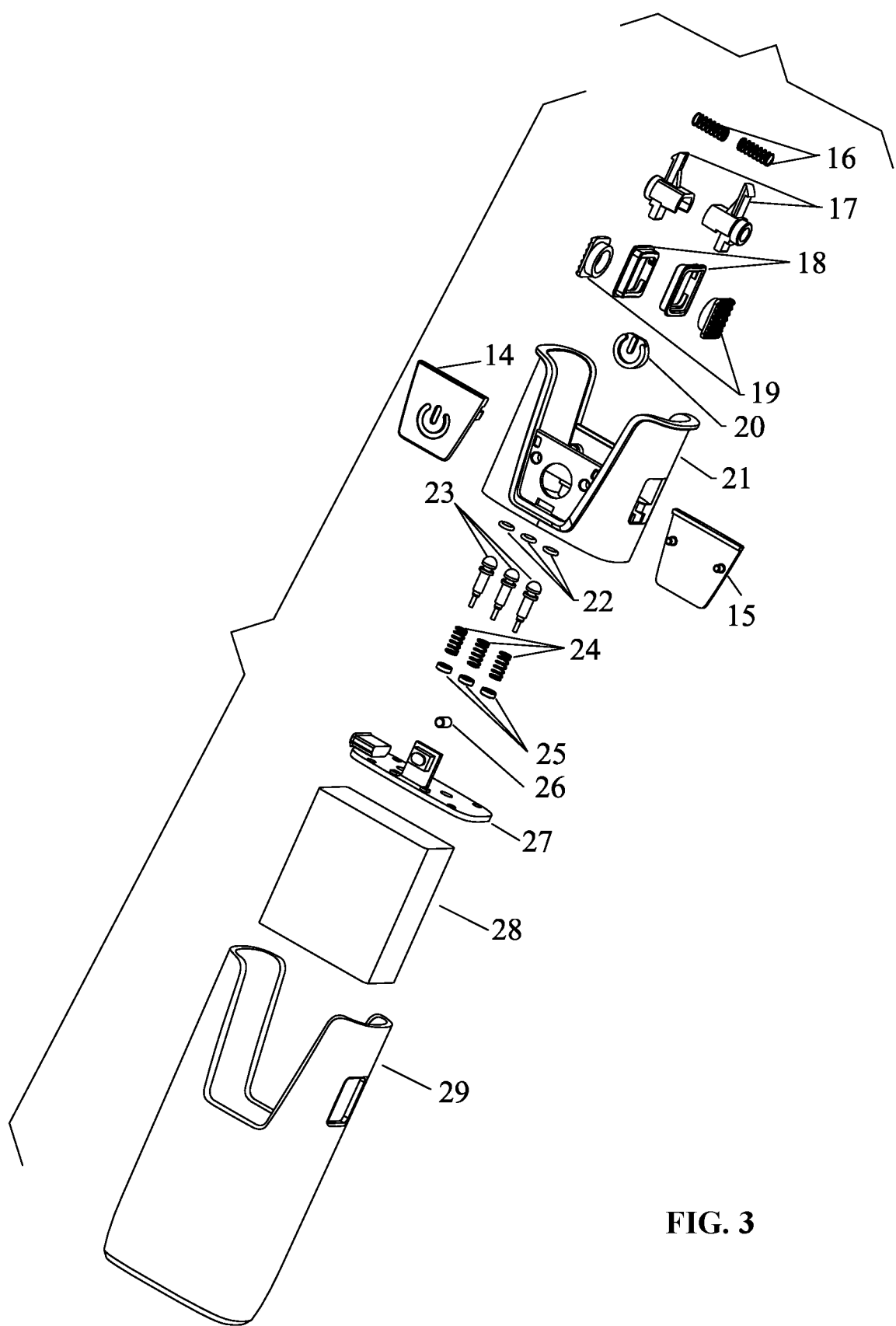
FIG. 3 is an exploded view of a battery assembly of an electronic cigarette as described in the disclosure.
Figure 4:
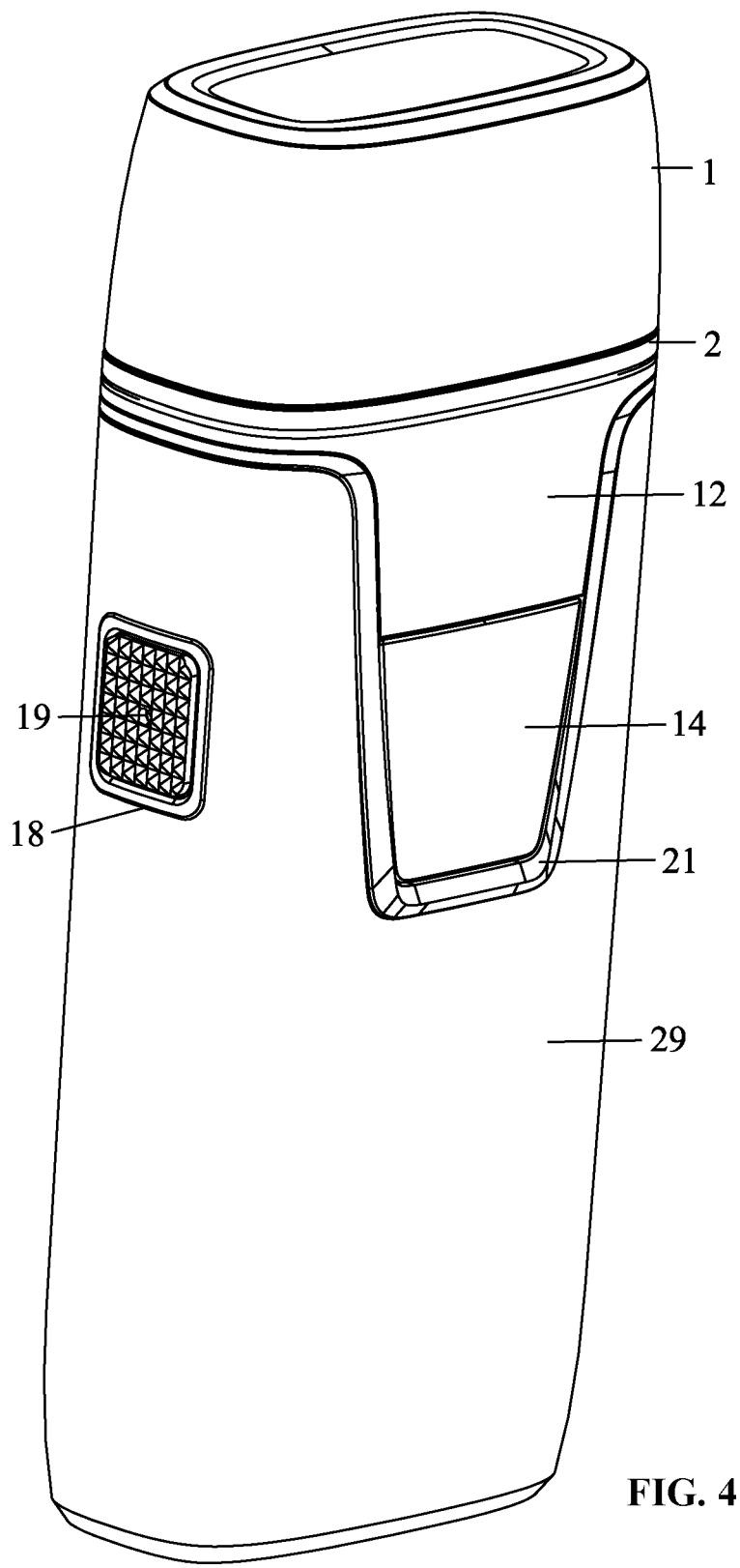
FIG. 4 is a stereogram of an electronic cigarette as described in the disclosure.
Figure 5:
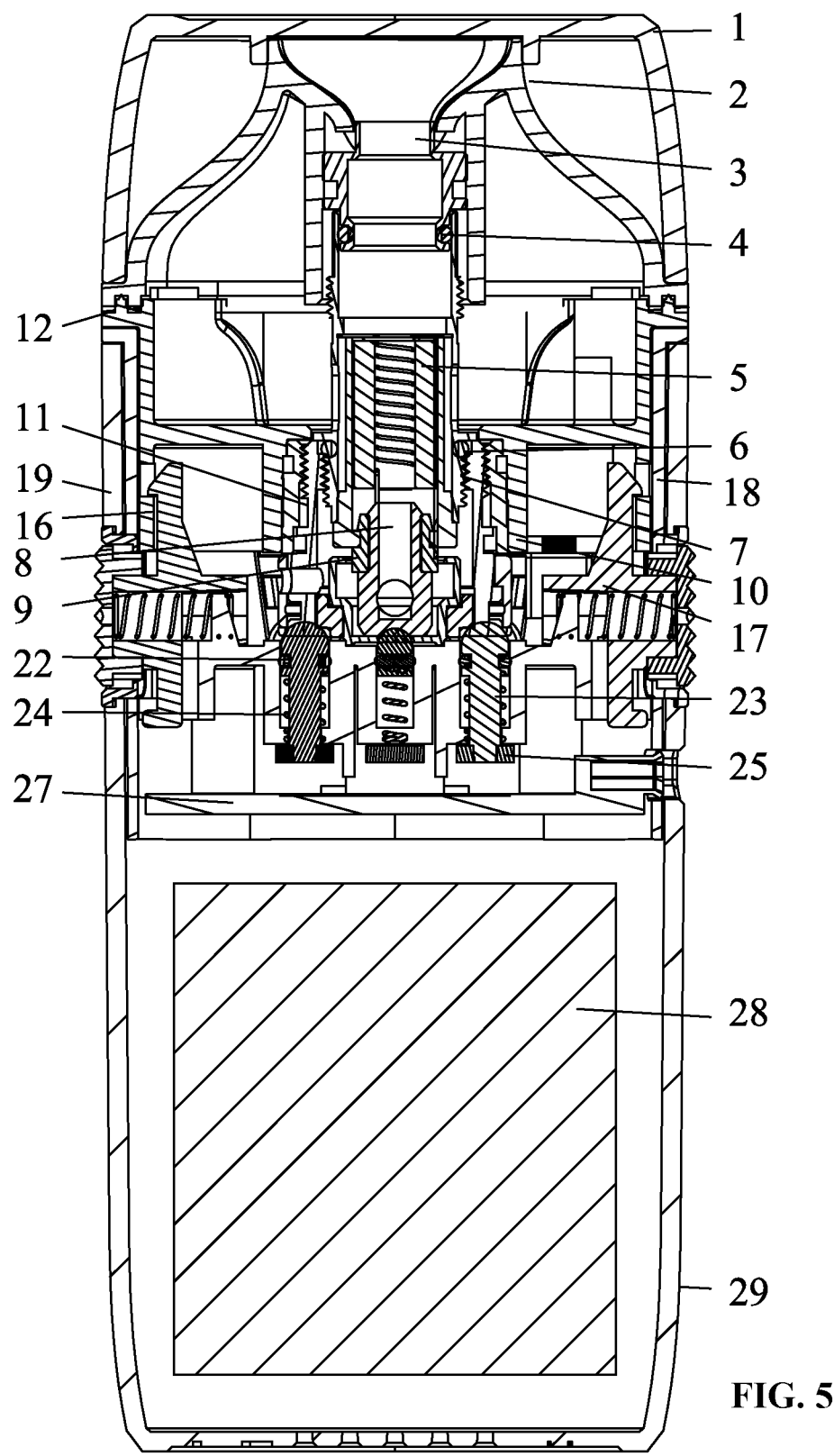
FIG. 5 is a sectional view of an electronic cigarette as described in the disclosure.

As shown in FIGS. 1-5, provided is an electronic cigarette, comprising: an atomizing assembly A; and a battery assembly B. The atomizing assembly A is disposed on the battery assembly B.

The atomizing assembly A comprises a mouthpiece cover 1, a mouthpiece 2, a seal holder 3, a first seal ring 4, an atomizing core 5, a silica ring 6, a first fixed seat 7, a joint 8, an insulation seat 9, a regulating ring 10, a fixed screw 11, an e-liquid container 12, an e-liquid feeder 30, a second seal ring 31, a first spring 32, an e-liquid guider 33, and a plug 13.

The battery assembly B comprises a button 14, a decoration cover 15, second springs 16, switch buttons 17, a decoration ring 18, a button cap 19, a light guide 20, a second fixed seat 21 adapted to fixing a printed circuit board, output electrodes 23, a third seal ring 22 adapted to seal the output electrodes 23, third springs 24, fixed rings 25 adapted to fix the output electrodes 23, a silica plug 26, a mainboard 27, a battery cell 28, and a base support 29.

The first seal ring 4 is disposed on the seal holder 3; the seal holder 3 is inserted in the mouthpiece 2; the joint 8 is fixed on the insulation seat 9; the insulation seat 9 is disposed in the first fixed seat 7. The silica ring 6 and the regulating ring 10 are disposed on the first fixed seat 7; the atomizing core 5 is inserted in the first fixed seat 7; the fixed screw 11 is disposed on a bottom wall of the e-liquid container 12; the mouthpiece 2 is disposed on the e-liquid container 12; the mouthpiece cover 1 is disposed on the mouthpiece 2; the first fixed seat 7 is fixed on the fixed screw 11.

The second seal ring 31 and the first spring 32 are disposed on one end of the e-liquid feeder 30, and the e-liquid guider 33 is disposed on the other end of the e-liquid feeder 30; the e-liquid feeder 30 is fixed on the e-liquid container 12; the plug 13 is inserted in the e-liquid container 12; and the mouthpiece cover 1 covers the e-liquid container 12. Uncover the plug 13, the e-liquid can be injected into the e-liquid guider 33. The opening and closing of the e-liquid inlet of the e-liquid feeder 30 is controlled by pressing down the e-liquid guider 33 to elastically drive the e-liquid guide hole to move upward and downward, improving the sealing properties of the electronic cigarette. The regulating ring 10 comprises locating slots, and the first fixed seat 7 comprises stop pins corresponding to the locating slots, so that in the process of regulating the volume flow rate of the vapor, the atomization core will not detach, preventing the unwanted leakage of the e-liquid. To dismantle the electronic cigarette, press down the regulating ring 10 to enable the stop pins to be clamped in the locating slots, and then the atomizing assembly can be detached from the battery assembly, thus facilitating the replacement of the atomizing assembly.

The second springs 16 are disposed in the switch buttons 17, and the switch buttons 17 are fixed on two sides of the second fixed seat 21; the button cap 19 is disposed in the decoration ring 18; and the decoration ring 18 is fixed on the switch buttons 17.

The mainboard 27 and the battery cell 28 are disposed in the base support 29; the third seal ring 22 and the third springs 24 are disposed on the output electrodes 23; the output electrodes 23 is fixed on the second fixed seat 21 via the fixed rings 25; the second fixed seat 21 is disposed in the base support 29.

The decoration cover 15 is attached to the second fixed seat 21; the silica plug 26 is disposed on the mainboard 27; the light guide 20 is disposed in the button 14, and the button 14 is fixed on the second fixed seat 21.

The atomizing assembly communicates with the battery assembly via the switch buttons 17 disposed at two sides of the battery assembly. This simplifies the dismantling of the electronic cigarette and facilitates the replacement of the atomizing assembly. To dismantle the electronic cigarette, synchronously press the button caps 19 disposed at two sides of the battery cell, and then the atomizing assembly is ejected and detaches from the battery assembly, thus facilitating the replacement of the atomizing assembly. The battery cell separated from the atomizing assembly is V-shaped. The battery cell 28 is a built-in rechargeable battery cell 28. The electronic cigarette is lightweight and easy to carry.

It will be obvious to those skilled in the art that changes and modifications may be made, and therefore, the aim in the appended claims is to cover all such changes and modifications.

What is claimed is:

1. An electronic cigarette, comprising:
   an atomizing assembly, the atomizing assembly comprising a mouthpiece cover, a mouthpiece, a seal holder, a seal-holder seal ring, an atomizing core, an atomizing-core-seat silica ring, an atomizing-core seat, a joint, a joint seat, a regulating member, a threaded member, an e-liquid container, an e-liquid feeder, a liquid-feeder seal ring, a liquid-feeder spring, an e-liquid guider, and a liquid-container plug; and
   a battery assembly, the battery assembly comprising a light-guide button, a decoration cover, assembly-separating-button springs, assembly-separating buttons, a button-cap frame, a button cap, a light guide, a circuit-board seat adapted to fixing a printed circuit board, output electrodes, an output-electrode seal ring adapted to seal the output electrodes, output-electrode springs, fixed hoops adapted to fix the output electrodes, a mainboard silica plug, a mainboard, a battery cell, and a base support; wherein:
   the atomizing assembly is disposed on the battery assembly;
   the seal-holder seal ring is disposed on the seal holder; the seal holder is inserted in the mouthpiece; the joint is fixed on the joint seat; the joint seat is disposed in the atomizing-core seat;
   the atomizing-core-seat silica ring and the regulating member are disposed on the atomizing-core seat; the atomizing core is inserted in the atomizing-core seat; the threaded member is fixed to a bottom wall of the e-liquid container via a threaded connection; the mouthpiece is disposed on the e-liquid container; the mouthpiece cover is disposed on the mouthpiece; the atomizing-core seat is fixed to the threaded member via a threaded connection;
   the liquid-feeder seal ring and the liquid-feeder spring are disposed on one end of the e-liquid feeder, and the e-liquid guider is disposed on the other end of the e-liquid feeder; the e-liquid feeder is fixed on the e-liquid container; the liquid-container plug is inserted in the e-liquid container; and the mouthpiece cover covers the e-liquid container;
   the regulating member comprises locating slots, and the atomizing-core seat comprises stop pins corresponding to the locating slots;
   the assembly-separating-button springs are disposed in the assembly-separating buttons, and the assembly-separating buttons are fixed on two sides of the circuit-board seat; the button cap is disposed in the button-cap frame; and the decoration ring button-cap frame is fixed on the switch assembly-separating buttons;
   the mainboard and the battery cell are disposed in the base support; the output-electrode seal ring and the output-electrode springs are disposed on the output electrodes; the output electrodes are fixed on the circuit-board seat via the fixed hoops; the circuit-board seat is disposed in the base support; and
   the decoration cover is attached to the circuit-board seat; the mainboard silica plug is disposed on the mainboard; the light guide is disposed in the light-guide button, and the light-guide button is fixed on the circuit-board seat.

* * * * *